(12) United States Patent
Bernardi et al.

(10) Patent No.: US 9,746,407 B2
(45) Date of Patent: Aug. 29, 2017

(54) METHOD FOR DETECTING MOLECULAR INTERACTIONS

(75) Inventors: Thierry Bernardi, Perignat les Sarlievre (FR); Pascal Mayer, Marsat (FR); Jérôme Groelly, Beaumont (FR)

(73) Assignee: Biofilm Control, Saint-Beauzire (FR)

( * ) Notice: Subject to any disclaimer, the term of this patent is extended or adjusted under 35 U.S.C. 154(b) by 0 days.

(21) Appl. No.: 13/808,077

(22) PCT Filed: Jun. 30, 2011

(86) PCT No.: PCT/FR2011/051528
§ 371 (c)(1),
(2), (4) Date: Mar. 15, 2013

(87) PCT Pub. No.: WO2012/001312
PCT Pub. Date: Jan. 5, 2012

(65) Prior Publication Data
US 2013/0164736 A1    Jun. 27, 2013

(30) Foreign Application Priority Data

Jul. 2, 2010 (FR) ................................ 10 02810
Aug. 19, 2010 (FR) ................................ 10 56678

(51) Int. Cl.
| | |
|---|---|
| A61M 1/36 | (2006.01) |
| A61M 1/16 | (2006.01) |
| G01N 33/543 | (2006.01) |
| G01N 11/10 | (2006.01) |
| G01N 24/08 | (2006.01) |
| G01N 33/558 | (2006.01) |
| G01N 33/80 | (2006.01) |
| G01N 33/569 | (2006.01) |

(52) U.S. Cl.
CPC ....... *G01N 11/10* (2013.01); *G01N 33/54326* (2013.01); *G01N 33/558* (2013.01); *G01N 33/56938* (2013.01); *G01N 33/80* (2013.01)

(58) Field of Classification Search
CPC ...... C12P 19/34; C12P 21/02; G01N 2333/82; G01N 33/6803; G01N 33/6842
USPC ........................................................... 435/5
See application file for complete search history.

(56) References Cited

U.S. PATENT DOCUMENTS

| | | |
|---|---|---|
| 3,635,678 A | 1/1972 | Seitz et al. |
| 4,935,147 A | 6/1990 | Ullman et al. |
| 5,443,959 A | 8/1995 | Kikuchi et al. |
| 2008/0038769 A1 | 2/2008 | Bernardi et al. |

FOREIGN PATENT DOCUMENTS

| | | | |
|---|---|---|---|
| EP | 1 544 596 | | 6/2005 |
| EP | 1 544 596 A2 | | 6/2005 |
| FR | 2 866 706 A1 | | 8/2005 |
| FR | 2 883 296 A1 | | 9/2006 |
| JP | H06209794 A | | 8/1994 |
| JP | 2007 525216 A | | 9/2007 |
| JP | 2009 069070 A | | 4/2009 |
| WO | WO 01/86255 | | 11/2001 |
| WO | WO 01/86255 A1 | | 11/2001 |
| WO | WO2008102218 | * | 8/2008 |
| WO | WO2009083856 | * | 7/2009 |

OTHER PUBLICATIONS

Bernardi et al., Abstract, 2005, FR2866706 A1: pdf p. 1.*
Bernardi et al., FR2866706 A1, 2005: pdf pp. 1-19.*
Bernardi et al., Drawings, 2005, FR2866706 A1: pdf pp. 1-4.*
Bernardi et al., Claims, 2005, FR2866706 A1: pdf pp. 1-6.*
Thierry et al., "Microorganism culture medium viscosity measuring procedure consists of immersing magnetic particle, moving it with an external electromagnetic field and measuring degree of free movement", 2005, FR2866706(A1):(machine translation) pdf pp. 1-19.*
William A. Catterall, "Structure and regulation of voltage-gated $Ca^{2+}$ channels", *Annu. Rev. Cell. Dev. Biol.* 16:521-55 (2000).
Gregory M Dick and Johnathan D Tune, "Role of potassium channels in coronary vasodilation", Exp Biol Med (Maywood). Jan. 2010; 235(1):10-22.
Maria Cristina Mostallino et al., "Plasticity and function of extrasynaptic GABA(A) receptors during pregnancy and after delivery" Psychoneuroendocrinology, Dec. 2009; 34S Suppl 1:S74-83.

* cited by examiner

*Primary Examiner* — Janet L Andres
*Assistant Examiner* — Barry A Chestnut
(74) *Attorney, Agent, or Firm* — Patterson Thuente Pedersen, P.A.

(57) ABSTRACT

The present invention relates to a method for detecting molecular interactions in a solution. In particular, the present invention relates to a method for detecting interactions between two substances that are likely to interact with one another. The present invention can be used in particular in the field of scientific research and in the field of medical analysis.

14 Claims, 2 Drawing Sheets

METHOD FOR DETECTING MOLECULAR INTERACTIONS

PRIORITY CLAIM

This application is a National Phase entry of PCT Application No. PCT/FR2011/051528, filed Jun. 30, 2011, which claims priority from French Application No. 1002810, filed Jul. 2, 2010, and French Application No. 1056678, filed Aug. 19, 2010, the disclosures of which are hereby incorporated by referenced herein in their entirety.

FIELD OF THE INVENTION

The present invention relates to a method for detecting molecular interactions. In particular, the present invention relates to a method for detecting molecular interactions between at least two substances that can interact with one another.

The present invention is particularly applicable in the field of scientific research, in the medical field, particularly in analysis of biological samples.

In the description below, the references in parentheses (Ref.) refer to the list of references presented at the end of the text.

BACKGROUND OF THE INVENTION

In the medical and analytical field, there are many situations where it is useful, even necessary, to detect interaction events between molecules and/or objects like antibodies, cells, bacteria, viruses and macromolecules. For example, to detect bacterial contamination, an antigen/antibody test is frequently used.

To determine an individual's blood group, an affinity test between antibodies and the individual's red blood cells is frequently used, thus enabling the blood group of said individual to be determined.

In the state of the art, there are "simple" methods that can be done when substances to be detected are present in large quantity. For example, this can be a method comprising a mixture of substances to be detected with affinity substances, i.e., substances that can interact with the substances to be detected. The interaction leads to the formation of a precipitate or aggregate visible to the naked eye which reveals the result. In this way, for example, it is possible to type a blood group by adding antibodies to a drop of blood and observing whether or not a red blood cell aggregate forms.

There are also methods that allow measuring the viscosity variations in a medium that occur when affinity substances come together in this medium.

For example, document U.S. Pat. No. 3,635,678 (Ref 1) describes a method in which a single macroscopic (much larger than a micron) steel ball immersed in the fluid is suspended by a set of magnets, the movement of the suspended ball being measured by an optical system. When the viscosity of the medium increases, the amplitude of the ball's movement decreases over time; the objective is to deduce the blood coagulation speed.

One major drawback of the technique described in this document is the complexity of its implementation, since a ball must be kept in suspension. Furthermore, the moving ball, because of its size and mass as described in the patent, can break weak interactions that cause the viscosity variation and impede their detection. The method is not very sensitive and is limited to detecting relatively large viscosity variations. Moreover, to read the results, complex systems and reagents must be used.

Another system is described in document WO 01/86255 (Ref 2) comprising a microscope with which it is possible to observe movement of a particle suspended in a liquid. The viscosity of the liquid is deduced by phase shift of the second harmonic of the signal obtained from observing the particle in suspension in a liquid with the microscope.

Another variant of this approach is described in document EP 1,544,596 (Ref 3), which comprises oscillation of a magnetizable particle in a magnetic field to generate a signal and therefore obtain a result.

One of the major drawbacks of these methods is the complexity of their implementation and of monitoring the oscillation of a particle activated by a force applied in a periodic and controlled manner. The complex, costly and difficult to configure instrumentation, on the one hand, to start and maintain the oscillation of the particle and, on the other hand, to observe the periodic movement of the particle.

Moreover, these methods only allow measuring the changes in viscosity that must take place in the oscillation zone of the suspended particle. Moreover, the viscosity changes must be substantial to be detected. Thus, it is necessary to have solutions that contain a large quantity of affinity substances. These methods are therefore not very sensitive and do not permit satisfactory precision to be obtained for methods using antibodies, for example, or other specifically directed affinity substances to detect or assay.

Another commonly used method to detect affinity reactions is the ELISA technique and its many variations. It consists of:
- attaching onto a substrate a first antibody having an affinity with a substance,
- contacting the substance to be detected with the first antibody attached to its substrate for a given duration,
- rinsing away the substance that did not react with the antibody,
- contacting the substance bound to the antibody attached to the surface and a second antibody with an affinity for said substance,
- rinsing away the antibodies that did not react with the substance, and
- detecting the presence of the second antibody bound to the substance bound to the first antibody bound to the substrate.

Most often, the second antibody is bound to a marker that is directly detectable by a physical method, for example a fluorescent or magnetic marker, or to a marker bound to an enzyme, for example alkaline phosphatase or horseradish peroxidase, in order to detect the product of the reaction catalyzed by the enzyme from an appropriate substrate.

This method has several drawbacks, for example it requires many controlled washes, reducing its sensitivity. It also comprises many steps of manipulation by a person skilled in the art: conducting at least two affinity reactions, required marking of the second antibody with at least one sensitive and sophisticated marker, and using a complex device that is difficult to configure to detect and quantify the signal emitted by the marker. This method is therefore time-consuming and expensive, and requires complex instrumentation for its implementation.

Other methods have been developed to detect an affinity reaction that require only a single antibody, for example techniques based on surface plasmon resonance, piezoelectric balances, or even simple observation by microscope for some substances permitting it. To do this, the antibody is attached to a substrate appropriate for the detection method, the substance is contacted for a given time with the antibody attached to the substrate, and then the reading is done directly or after rinsing to remove the substances that did not have an affinity reaction with the antibodies.

These methods have many drawbacks; for example, the instrument required to do the reading is sophisticated and expensive. Moreover, they require special substrates for attaching said antibodies. Furthermore, they require a large number of steps and depend on the quality and quantity of antibodies attached.

In the above-mentioned methods, it is therefore essential to attach the antibody or any other affinity substance to a substrate. Affinity surfaces are known in the state of the art. Such surfaces may be obtained, for example, by "molecular molding".

It is also known that the above-named methods can be implemented by attaching the substance that one wishes to detect onto a substrate in a non-specific way. The substance thus attached will be contacted with an antibody or any other suitable affinity substance, possibly labelled, according to the detection method, and then possibly rinsed before being read.

However, these variants have many drawbacks. In particular, it is necessary to bind the substance to be detected onto the substrate, which is not possible in a universal or specific manner. Moreover, this attachment can change the structure of the substance attached. This structural change can alter detection sensitivity and/or specificity, in particular when antibodies are used. Moreover, the attachment can lead to obtaining false negative and/or false positive results. Moreover, the attachment may be different from one implementation to another, so the results thus obtained may not be reproducible. Moreover, complex and expensive devices are required for detection.

There is a thus real need to find a method for detecting molecular interactions alleviating these deficiencies, drawbacks and obstacles of the prior art, in particular, a method that improves the sensitivity of molecular interaction detection and reduces the costs of implementation, a method whose implementation is simple and which provides fast, reliable and reproducible results.

DESCRIPTION OF THE PRESENT INVENTION

The objective of the present invention is to respond to the numerous above-mentioned requirements and drawbacks of the prior art by providing a method for detecting molecular interactions.

In particular, the present invention relates to a method for detecting interactions in a solution comprising the following steps:
a. introducing into a solution at least one first substance and preferably at least one second substance that can interact with said first substance,
b. introducing into the solution obtained in step a) at least two magnetic or magnetizable particles, said particles resting on a surface immersed in said solution,
c. determining the interaction of said substances by application of an electric, magnetic or electromagnetic field designed to set said particles in motion, the interaction between said substances being detected when the mobility of said particles on said surface is changed.

According to the invention, mobility means the movement of the particles by application and/or under the effect of the electric, magnetic or electromagnetic field. This mobility can be defined, for example, from the ratio of the particle speed at a given point in space and the intensity of the gradient of the square of the magnetic field in this given point in space, for example from the ratio of the particle speed at a given point in space and the intensity of the electric potential gradient at this given point in space.

According to the invention, the mobility shift can be chosen from braking, slowing, change in trajectory, acceleration or stoppage of said particles.

Thus, according to the invention, the application of the electric, magnetic or electromagnetic field can induce said particles to cluster, not cluster or disperse.

According to the invention, interaction of substances means, for example, a molecular interaction such as hydrogen, ionic, or van der Waals bonding interactions, a biological interaction, for example, specific three-dimensional hormone-receptor pattern recognition or antibody-antigen interactions, an electrostatic interaction, a magnetic interaction, a concentration gradient of ions or molecules, in other words, any potential, molecular or ionic concentration gradient that originates at the substances and which tends to make them move together or apart, for example via hydrogen bonds, van der Waals interactions, hydrophobic bonds, covalent bonds, ionic bonds, for example by chemotaxis movement. For example, it can be antigen-antibody, enzyme-substrate, receptor-ligand, molecule-cell, cell-vector, cell-virus, eukaryote cell-prokaryote cell, eukaryote cell-eukaryote cell, or prokaryote cell-prokaryote cell interaction.

The solution that can be used in the present invention may be a liquid or gaseous solution. The solution may be any solution known to a person skilled in the art. It may be, for example, a culture medium, such as a eukaryotic and/or prokaryotic cell culture medium, a buffer medium, for example any buffer medium known to a person skilled in the art, for example a commercially available buffer medium like phosphate buffered saline (PBS), a biological sample, for example a sample of blood, plasma, urine, cerebrospinal fluid, a saline solution, for example physiological solution, a culture medium, for example a brain-heart infusion available commercially, a solvent, for example acetone, dimethyl sulfoxide, ethanol, methanol, propanol, acetonitrile, ethyl acetate, ether, phenol, chloroform, tetrahydrofuran, difluoroethylene, and/or a hydrocarbon, for example hexane, cyclohexane, benzene, octane, decane, oil, gasoline or diesel fuel.

According to the invention, the gas may be, for example, air, oxygen, nitrogen, neon, argon, $CO_2$, methane or ozone.

According to the invention, a liquid solution can have a density of 0.1 to 4 kg/l or 0.3 to 3 kg/l; a gas solution can have a density of $10^{-15}$ kg/m$^3$ to 1000 kg/m$^3$, $10^{-10}$ to 30 kg/m$^3$ or $10^{-5}$ to 3 kg/m$^3$.

A person skilled in the art will easily determine the density of a solution from this general knowledge. For example, the density of the solution can be measured, for example, by measuring the ratio of the mass over the volume, for example by weighing a solution of known volume.

According to the invention, the solution can be treated beforehand, for example, the sample may be purified, diluted or concentrated.

According to the invention, the solution may be purified by any method known to a person skilled in the art, for example dialysis, filtration, ultrafiltration, clarification and centrifugation. For example, the filtration method may include passing the solution through a screen with 0.2 to 100 µm pores, the ultrafiltration method may include, for example, centrifugation at a rate of 1 to 3000 rpm for a time of 0.1 to 30 minutes, the dialysis method may be, for example, a method including a step of depositing the solution on a dialysis membrane, for example at a cut-off threshold of 500 Da, said membrane floating on the distilled water contained in a container. The clarification method may be, for example, a method comprising the addition of 0.1% (weight/weight) of bovine serum albumin into the solution.

According to the invention, purifying the solution can advantageously eliminate any contaminant and/or molecule from the solution that may affect the detection of the molecular interaction, for example purification can independently eliminate bacteria, viruses, proteins, chemical molecules, salts, particulates or molecule aggregates. Of course, a person skilled in the art, from this general knowledge, would know how to adapt the purification method according to the solution.

According to the invention, the solution may also be diluted, for example any method known to a person skilled in the art, for example by serial dilution. The solution may be diluted with any diluent known to a person skilled in the art. This may be, for example, a buffer solution, for example phosphate buffered saline, a saline solution, for example physiological saline, ethanol, DMSO, acetone, hexane and/or any hydrocarbon solvent or solution described previously.

The solution may be diluted, for example by a factor of 2 to 20 000, 5 to 500 or 5 to 50.

Diluting the solution may advantageously enable the concentration of components present in the solution to be changed, for example, by reducing the concentration, for example dilution may reduce the protein concentration. Dilution may also reduce the concentration of any interfering compounds and thus advantageously improve the specificity and/or sensitivity of the method of the invention.

According to the invention, the solution may also be concentrated, for example by any method known to a person skilled in the art, for example by ultracentrifugation, ultrafiltration, evaporation or lyophilization.

According to the invention, the purification, dilution and/or concentration of said solution may advantageously enable the density of said solution to be adjusted.

Adjusting the density of the solution advantageously enables the specificity and/or sensitivity of the method of the invention to be improved, notably by increasing, decreasing or canceling the effect of the force of gravity that pushes the particles toward the surface.

According to the invention, the volume of solution used in the method may be for example, 0.3 µl to 100 ml, 3 µl to 10 ml, or 30 µl to 1 ml.

According to the invention, the solution may be able to modulate the interaction between said first and said second substance. For example, the solution may increase or decrease the interaction between said substances.

According to the invention, the solution may advantageously include a compound that increases or decreases the interaction between said first and second substances. The compound may be added into the solution, for example, prior to implementing the method of the invention. The compound may be, for example, chemical molecules, salts, ions, polymers of macromolecules, colloids, microparticles, for example acids and bases that change the pH of the solution, for example NaCl, which changes the ionic strength of the solution, for example polyethylene glycol, which may for example, increase the affinity of said substances.

The present invention advantageously permits determining whether said solution effectively modulates the interaction by comparison of the results obtained by the method of the invention in which the substances are identical with different solutions.

According to the invention, the first substance may be chosen from the group comprising eukaryotic cells, prokaryotic cells, membranes, viruses, prions, mitochondria, chloroplasts, vesicles, liposomes, cell constituents, flagella, proteins, lipoproteins, glycoproteins, antibodies, nucleic acids, lipid complexes, colloids, macromolecules, microparticles, nanoparticles, antigens, hormones, protein ligands and chemical molecules.

According to the invention, the eukaryotic cells that can be used in the present invention may be, for example, animal eukaryotic cells, for example blood cells, for example leukocytes, for example granulocytes, neutrophils, eosinophils, basophils, B cells, T cells, NK cells, monocytes, erythrocytes or thrombocytes. They may also be plant eukaryotic cells, for example plant epidermal cells, xylem, phloem, parenchyma, collenchyma or sclerenchyma. They may also be fungi or yeasts. For example, they may be *Candida, Cryptococcus, Malassezia, Pityrosporum, Pneumocystis, Epidermophyton, Microsporum* or *Trichophyton*. They may also be protozoa, for example *Entamoeba histolytica, Acanthamoeba castellanii* or *Naegleria fowleri*.

According to the invention, the prokaryotic cells may be, for example, any bacteria known to a person skilled in the art. The bacteria that may be used in the present invention are, for example, bacteria comprised in the group, without being limited thereto, consisting of: *Acetobacter aurantius, Actinobacillus actinomycetemcomitans, Agrobacterium tumefaciens, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus stearothermophilus, Bacillus subtilis, Bacteroides gingivalis, Bacteroides melaminogenicus, Bartonella henselae, Bartonella quintana, Bordetella bronchiseptica, Bordetella pertussis, Borrelia burgdorferi, Branhamella catarrhalis, Brucella abortus, Brucella melitensis, Brucella suis, Burkholderia mallei, Burkholderia pseudomallei Calymmatobacterium granulomatis, Campylobacter coli, Campylobacter jejuni, Campylobacter pylori, Chlamydia pneumoniae, Chlamydia psittaci, Chlamydia trachomatis, Chlamydophila pneumoniae, Chlamydophila psittaci, Clostridium botulinum, Clostridium difficile, Clostridium perfringens, Clostridium tetani, Clostridium welchii, Corynebacterium diphtheriae, Corynebacterium fusiforme, Coxiella burnetii Ehrlichia chaffeensis, Enterococcus avium, Enterococcus durans, Enterococcus faecalis, Enterococcus faecium, Enterococcus galllinarum, Enterococcus maloratus, Escherichia coli Francisella tularensis, Fusobacterium nucleatum Gardnerella vaginalis Haemophilus ducreyi, Haemophilus influenzae, Haemophilus parainfluenzae, Haemophilus pertussis, Haemophilus vaginalis, Helicobacter pylori Klebsiella pneumoniae, Klebseilla rhinoscleromatis-klebsiella oxytoca Lactobacillus acidophilus, Lactobacillus casei, Lactococcus lactis, Legionella pneumophila, Methanobacterium extroquens, Microbacterium multiforme, Micrococcus luteus, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma pneumoniae Neisseria gonorrhoeae, Neisseria meningitidis, Nocardia asteroides Pasteurella multocida, Pasteurella tularensis, Porphyromonas gingivalis, Pseudomonas aeruginosa, Pseudomonas malto-*

*philia, Rhizobium radiobacter, Rickettsia prowazekii, Rickettsia mooseri, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Vibrio cholerae, Vibrio comma, Vibrio parahemolyticus, Vibrio vulnificus, Xanthomonas maltophilia Yersinia enterocolitica, Yersinia pestis* and *Yersinia pseudotuberculosis*, etc.

The membranes that can be used in the present invention may be any fragment of eukaryotic or prokaryotic cell membranes, for example the above-named eukaryotic or prokaryotic cells, any cell membrane and/or cell compartment fragment, for example mitochondria, chloroplasts, endoplasts or endoplasmic reticulum.

The proteins that can be used in the present invention may be plasma proteins, cell proteins or bacterial proteins. For example, the proteins may be hormones, for example progesterone, vasopressin, thyrotrophic hormone, luteinizing hormone (LH), thyroid-stimulating hormone (TSH), growth hormone (GH), epidermal growth factor (EGF), insulin or oxytocin. They may, for example, be channels, for example calcium channels, for example the channels described in Catterall W A. (2000) Structure and regulation of voltage-gated $Ca^{2+}$ channels. *Annu. Rev. Cell. Dev. Biol.* 16:521-55 (Ref 4), potassium channels, for example the channels described in Dick G M and Tune J D, Role of potassium channels in coronary vasodilation, Exp Biol Med (Maywood). 2010 January; 235(1):10-22. (Ref 6). They may also be peptides involved in the major histocompatibility complex (MHC), for example MHC I and MHC II. They may also be receptors, for example nuclear, intracellular, membrane, transmembrane, or g-protein coupled receptors, acetylcholine receptors, FSH receptor, testosterone receptor, for example the receptor described in Mostallino M C et al., Plasticity and function of extrasynaptic GABA(A) receptors during pregnancy and after delivery, Psychoneuroendocrinology. 2009 December; 34 Suppl 1:S74-83 (Ref 7). They may also be enzymes, for example bacterial enzymes, for example restriction enzymes, for example HindIII, Eco RI, BamHI, MstII, TaqI, NotI, Hinfl, AluI, BgIIII, HaeII, HhaI, PstI or SmaI, enzymes involved in cell signaling, for example protein kinases, enzymes involved in biosynthesis, for example biosynthesis of fatty acids, phosphorylases, dehydrogenases, for example glucose dehydrogenase, or enzymes involved in general metabolism, for example aldehyde dehydrogenase, alpha-amylase, L-gulonolactone oxidase, rhodopsin, cytochrome B or cytochrome C. They may also be structural proteins, for example actin, myosin, peptin, albumin, collagen or histone H4.

The antibodies that can be used in the present invention may be any antibody known to a person skilled in the art. For example, they may be any commercially available antibody, for example IgG, IgA, IgM, IgE and IgD, the antibodies may be for example, antibodies directed against one of the above-mentioned proteins, antibodies directed against another antibody, for example rabbit antibodies directed against human antibodies, for example antibodies directed specifically against antibodies directed against the FSH receptor. They may also be antibodies obtained after immunization of an individual, for example according to the method described in the document Biologie cellulaire et moléculaire, Concepts et expériences, [Molecular and cellular biology, concepts and experiments] $2^{nd}$ edition 2004, Gerald Karp (Ref 5). They may be, for example, antibodies produced by a human or animal in response to an infection, for example by a virus, bacteria, prion, parasite, protozoa, as well as in response to a disease, for example cancer, an autoimmune disease such as, for example, Graves' disease, multiple sclerosis, as well as in response to intoxication, poisoning, contamination, doping, ingestion, inhalation and injection, for example of a pesticide, poison, insecticide, herbicide, allergenic agent as well as in response to a transplant, for example of bone marrow, of an organ such as, for example, a kidney, lung or liver, a limb such as a hand, leg or foot, as well as in response to implantation of an artificial organ, implantable port, pacemaker, artificial heart or artificial hip.

The chemical molecules that can be used in the method of the invention may be any chemical molecule known to a person skilled in the art. They may, for example, be a coagulation reagent, a reagent described in the document, a hormone, for example steroid hormones, for example cortisol, aldosterone, progesterone, dehydroepiandrosterone (DHEA), dehydroepiandrosterone sulfate (DHEAS), estradiol, androstenedione, dihydrotestosterone (DHT), estrone, estriol, testosterone, for example thyroxine, for example peptide hormones, for example erythropoietin (EPO), glucagon, somatostatin, atrial natriuretic peptide (ANP), or adrenocorticotropic hormone (ACTH).

According to the invention, the first substance may be present in the solution; in this case, the first substance does not need to be introduced into the solution.

According to the invention, said first substance may be attached onto the immersed surface beforehand. The method for attaching the first substance that can be used in the present invention may be any method known to a person skilled in the art. Of course, a person skilled in the art, from this general knowledge, would know how to choose the attachment method according to the first substance.

According to the invention, when the first substance is attached, the molecular interaction with said second substance changes the immersed surface and, for example, may densify this surface on which said braking particle rests so the movement of said particle when the electric, magnetic or electromagnetic field is applied thus reveals the interaction.

According to the invention, the second substance may be any substance defined above that can interact with the first substance.

According to the invention, the density of the first and/or the second substance may be greater or less than that of the solution, preferably greater than that of the solution. Advantageously, the superiority of the density of said first and/or said second substance allows locating said first and/or said second substance near the bottom of the container.

According to another embodiment of the invention, the method of the invention can be implemented with a solution previously containing said at least one first or said at least one second substance. In this embodiment, the method may not comprise step a) and may only comprise above-mentioned steps b) and c).

According to the invention, the method may comprise, instead of step a)

a prior step a') of attaching said first substance onto a surface of a container, a") introducing a solution into said container, and a''') introducing at least one second substance that can interact with said first substance.

According to the invention, the method of the invention can be implemented with a plurality of particles, for example, with at least two particles, with, for example, 2 to 10 000 000, 1000 to 1 000 000, 10 000 to 1 000 000, 100 000 to 1 000 000 or 10 000 to 100 000. The plurality of particles advantageously enables directly detecting, without a complex visualization device and without dye, the interaction between said substances, unlike the methods of the prior art using a single particle and requiring complex visualization devices or dyes for detecting interaction.

According to the invention, said at least two particles may be chosen in the group comprising electrically charged particles, magnetic particles, particles coated with at least one magnetic layer, magnetizable particles, particles coated with a magnetizable layer, electric, electromagnetic or electrifiable particles bearing an electrical charge or a mixture of two or more of these particles. They may be, for example, particles entirely or partially made up of a magnetic or magnetizable material, i.e., that can be set in motion by the effect/application of an electric, magnetic or electromagnetic field. Indeed, they may be any particle enabling the present invention to be implemented.

Advantageously, said particles may be a particle in any form suited to the implementation of the present invention, for example in the form of a ball, puck, asymmetrical geometric shape, for example with a flat face, etc.

Any appropriate size of magnetic particle may be used. The size may be chosen, for example, according to the size of the solution container. For example, the size of the particles may be less than a tenth of the size of the container, preferably less than a hundredth, more preferably still less than a thousandth of the size of the container. For example, the particle may have a size of 10 nm to 100 µm or 0.1 to 10 µm.

Advantageously, the method of the invention enables fine variations to be measured in the viscoelastic properties of the solution in which the particles are immersed. The lower this variation, the more sensitive the measurement must be. By using a plurality of particles, the invention precisely and advantageously enables small variations to be detected caused by weak interactions between substances that are either in small quantities or implement low intensity interaction forces. The use of a single particle and/or magnetic or magnetizable ball does not satisfactorily enable the interactions to be detected. Moreover, there is a non-negligible risk of detecting non-specific phenomena, for example caused by the presence of an aggregate or impurities that can interfere with the movement of said magnetizable microparticle under the effect of the magnetic, electric or electromagnetic field.

In contrast, the method of the invention in which at least two particles are used gives a reliable and statistically representative result.

Moreover, the higher the number of particles, the more information their relative movements provide, particularly by permitting a better coverage of the surface in contact with which the phenomenon measured is developed. The method of the invention therefore advantageously permits interpreting not only the movement of said microparticles themselves (trajectory, movement speed), but also the overall picture they will draw after application of the magnetic, electric or electromagnetic field. Indeed, the initial homogenous distribution of a plurality of microparticles is disrupted by the application of this field in accordance with the viscoelastic properties of the medium. For example, if the medium is very viscous, for example if strong interactions between the substances brought into contact occur therein, the distribution remains homogeneous since the particles cannot move much or at all under the effect of said field. If the medium is not very viscous or not viscous at all, or if very weak or null interactions between said substances brought into contact occur therein, the distribution will follow the strongest field lines, for example by forming a ring or spot above a cylindrical magnet, since the particles are free to move under the effect of said field.

Moreover, the method of the invention also advantageously makes it possible, by using a plurality of particles, for example by distributing and/or dispersing said particles homogenously in the solution containing said substances, to visually observe the interactions visible not only on the molecular scale, i.e., around a nanometer, but also on the microscopic scale, i.e., around a micron, and even on the macroscopic scale, i.e., larger than a micron.

For example, interactions between substances leading 1) to the formation of aggregates, nucleation cores or crystals, interfere in different ways with said particles in comparison with substances whose interactions lead 2) to the formation of more or less crosslinked polymers. In the first case, the particles tend to accumulate against the aggregates, nucleation cores or crystals on the side opposite the direction of movement generated by application of the electric, magnetic or electromagnetic field on said particles. The particles generate a contrasted image at the areas of accumulation. In the second case, if polymerization occurs homogenously and regularly in the solution, the image reflects the progressive immobilization of said particles as the intensity of the electric, magnetic or electromagnetic field decreases (for example, in proportion to the distance from the magnet). The method of the invention therefore advantageously enables images to be obtained revealing the structures resulting from interactions between the substances and the particles in the solution.

Preferably, the number of particles used to visualize the images on the microscopic and even the macroscopic scale is from 1000 to 1 000 000, 10 000 to 1 000 000, 100 000 to 1 000 000, or 10 000 to 100 000.

According to the invention, the particles may advantageously have a density near the density of the substances that can interact with them. For example, the particles may have a density relative to the substances comprised between 0.3 and 3.

According to the invention, the density of the particles may be determined by any method known to a person skilled in the art, for example, it may be the ratio between the particle mass and the increase in volume of the solution into which these particles are added.

According to the invention, the density of the particles advantageously improves the specificity and/or sensitivity of the method of the invention, for example by increasing, decreasing or canceling the effect of gravity.

Preferably, the particles and the substances will have a density higher than that of the solution in which they are contained. Preferably, the particles and the substances will have a density slightly higher, for example from 1.0001 to 3 times higher than that of the solution in which they are contained.

Advantageously, adhesion molecules may be coupled to the surface of the particles. Advantageously, the coupling of said molecules to the surface of the particles helps the particles to adhere together. For example, the particles may be covered with polymers, for example block polymers comprising a hydrophilic part and a hydrophobic part, advantageously permitting fixed clustering of the particles after the electric, magnetic or electromagnetic field is applied. In other words, the interaction between the adhesion molecules joins the particles together after the field is applied, and therefore gives a stable and non-modifiable result.

According to the invention, the particles may be of identical or different sizes.

When the particles are of identical sizes, the particles are essentially braked or accelerated at the same time during the molecular interaction. When the particles used have different sizes, the size of the small particles may be chosen, for example, so that they are braked as soon as the molecular interaction begins and the large particles are braked later. In this case, the smallest particles are braked before the largest particles.

When the particles are of different sizes, the small particles may have a size, for example, from 10 nm to 1 µm, for example from 100 to 500 nm, and the large particles may have a size, for example, from 1 µm to 100 µm, for example from 1 µm to 10 µm, for example from 1 µm to 5 µm.

Advantageously, particles of varied sizes may permit early and more sensitive detection and/or analysis of molecular interaction.

According to the invention, a plurality of particles of identical sizes with different magnetization may also be used.

The difference in behavior of the various particles can advantageously enable the strength of the molecular interaction to be evaluated. By applying the magnetic field can induce movement of the most strongly magnetized particles, the magnetic force is greater, while the particles that were more weakly magnetized cannot be set in motion, in comparison with total immobilization of all particles when the interaction is strong.

According to the invention, said at least one particle is preferably a particle generating a detectable signal. The detection of this signal will depend on the properties of the particle. For example, said at least one particle may be fluorescent, phosphorescent, radioactive, chemiluminescent, reflective or colored.

For example, in the case where said at least one particle is fluorescent, the fluorescence emitted by said particle may be detected, for example, visually and/or by any optical means known to a person skilled in the art. Said at least one particle may be, for example, illuminated to follow its movement by means of a light source, for example a laser beam.

According to the invention, the illumination may be continuous or intermittent. For example, the illumination may be done throughout the method or, for example, during step a) or b) or c), a) and c), a) and b) or b) and c).

For example, in the case where said at least one particle is phosphorescent, said particle may be displayed, for example, visually and/or by any optical means known to a person skilled in the art.

For example, in the case where said particle is radioactive, said particle may be detected even through optically opaque liquids or culture media, as well as through optically opaque microdilution plates by any radioactivity emission detection device known to a person skilled in the art, particularly the conventional method of revelation on autoradiographic film. It is then sufficient to flatten the sensitive film under the microdilution plate and then reveal the image at the bottom of said microdilution plate.

For example in the case where said at least one particle is chemiluminescent, said particle can be detected by adding the chemical reagent into the medium to permit said particle to emit luminous energy. The detection of this signal may be, for example, visual and/or by any means known to a person skilled in the art, notably by the use of a CCD (charge coupled device) camera sensitive to the wavelengths emitted, which scan the wells of the microdilution plate.

For example, in the case where said at least one particle is reflective, said particle may be detected, for example, visually or by any optical means known to a person skilled in the art. Advantageously, said at least one particle may be, for example, illuminated to follow its movement by means of a light source, for example by a laser beam.

For example, in the case where said at least two particles are colored, said particles may be detected, for example, visually and/or by any optical means known to a person skilled in the art for the detection of colored particles.

According to the invention, said particles may advantageously be chosen in different colors depending on their size and/or magnetic power. The application of the magnetic field in this case causes a colored point or ring or colored spot to appear on the surface by clustering said particles. This characteristic advantageously enables the clustering to be visually detected more easily. Indeed, for example in the case where said particles have different sizes, the large particles having one color and the small ones having another, when the magnetic field is applied, if the interaction between said substances is weak, the small particles remain immobilized in the solution, while the large particles are clustered. This clustering is visible by the appearance of a colored point which, in this case, is identical to the color of the largest particles. If no molecular interaction is present in the solution between the substances, the small and large particles may be clustered and the clustering of particles is visualized by the appearance of a colored point corresponding to the superimposition of the two colors. Finally, if the molecular interaction is substantial, the particles may be completely braked and therefore may not be clustered and no colored point is visible.

In other words, clustering may be evaluated, for example, by measuring the spot formed by said clustered particles. For example, when said particles are colored, by measuring the color of said particles. Moreover, clustering may be evaluated, for example, as a function of the form of the spot obtained, for example as a function of the shape, diameter or its topology, for example a disk or a ring.

A person skilled in the art will easily understand that for the embodiment of the present invention, the visual properties of said at least two particles may also be chosen according to the solution. Indeed, detecting the movement of said at least two particles is all the more easier the greater the contrast between the color of said at least two particles and the color of the solution.

In the present invention, the magnetic, electric or electromagnetic field may be any field that causes said at least two particles to move on said surface immersed in said solution, for example an electromagnetic field or a magnetic field. The magnetic, electric or electromagnetic field may be generated, for example, by a magnet or a solenoid. The magnet may be, for example, in the form of a bar, spike, part, etc. or any other appropriate shape for implementing the present invention. The field may be applied, for example, by any means known to a person skilled in the art, for example by pulses, by progressive increase of the electromagnetic field, by variations in the electromagnetic field or by a combination of these applications.

A progressive increase in the electromagnetic field may be obtained, for example, by moving a magnet closer along a straight or sinusoidal trajectory, or by an oscillating movement, with or without a variable amplitude of oscillation and/or frequency. More complex field variations may be obtained, for example by rotation or by combinations of movements of a magnetic material near said at least one particle.

Thus, according to the invention, said magnetic field may be generated by field-generating means which may or may not be moving.

When several particles must be set in motion, the field must be able to cluster said particles on said surface immersed in said solution.

Regardless of the implementation of the invention, the method of the invention may advantageously be conducted simultaneously in a plurality of compartments.

In this case, for setting the particles in motion in said compartments, a plurality of magnetic fields, for example magnets, may advantageously be used. The magnets may be attached, for example, onto a substrate so that each compartment in which the method of the invention is conducted can be juxtaposed with a magnet of the substrate. The application of the magnetic field on said compartments is independent from one compartment to another. The magnetic field applied to said compartments may be identical or different from one compartment to the other, preferably identical.

According to the invention, the magnetic, electromagnetic or electric field may be applied, for example, for a time of 1 second to 15 minutes or 10 seconds to 10 minutes. Of course, a person skilled in the art, from this general knowledge, will know how to adjust the time in accordance with the substances tested and/or the power of the field applied.

In the present invention, compartment means, for example, a culture reactor, wells or tubes, for example, of microdilution plates. Microdilution plate means the type of plate defined, for example, by the American National Standards Institute and the Society for Biomolecular Sciences (microplates) bearing 96, 384 and even 1536 wells.

The material making up said compartment may be any material suited to the embodiment of the present invention, for example plastic, for example polycarbonate, polystyrene, etc., glass, metal, etc. Advantageously, polystyrene microdilution plates can be used with bottomless wells. The bottom of these wells is created by fixing a flat surface under the microdilution plate. This flat surface may be made of transparent materials, for example, plastic, glass, etc. or opaque materials, for example metal, ceramic, etc. The flat surface can be attached under the microdilution plate by any appropriate method known to a person skilled in the art for such attachment, for example by gluing with an adhesive, by a friction method, by fusion bonding of the plastic, for example with a laser, etc.

According to the invention, the various compartments may be grouped on a same substrate, for example, on a plate with 1 to 1536 wells, for example 6, 16, 64, 96, etc.

The compartment may be, for example, a chamber with one end closed, like a tube, well etc., or a chamber with two openings.

According to a first configuration, the compartment may have one end closed so as to form a flat bottom.

According to a second configuration, the compartment may have one end closed so as to form a hemispheric bottom.

According to the invention, the interaction between said substances may be determined directly after application of the magnetic, electromagnetic or electric field. For example, the interaction may be determined from 0.01 second to 30 minutes or from 1 second to 3 minutes after application of the field.

According to the invention, the interaction between said substances may also be determined by comparing the clustering of particles when the magnetic, electromagnetic or electric field is applied. For example, it is possible to compare the clustering of particles in a solution containing none or only one of said above-mentioned substances with the clustering of particles in a solution containing said first and said second substance. If the clustering is greater or lesser in the solution containing none or only one of said substances then said substances interact and this interaction is thus determined. In other words, the interaction between the substances may decrease or increase the clustering of the particles when said field is applied and may thus be determined. For example, if the interaction causes the substances to aggregate, the medium may become less viscous and the clustering of particles will be increased. For example, if the interaction causes the substances to precipitate, the surface may be, for example, encumbered by the precipitate and the clustering of the particles will be decreased. For example, if the interaction causes the substances to crosslink, the network of substances will slow the particles and the clustering of particles will be decreased. For example, if the interaction causes the formation of linear chains of substances then the viscosity of the medium will be increased and the clustering of the particles will be decreased.

According to the invention, the method may be conducted, for example, in a plurality of compartments each containing said solution, said at least one particle, and said substances that can interact.

According to the invention, the method may also comprise a mixing step b'. Mixing can be done, for example, by stirring the solution in which said substances are present. It may be, for example, mixing with a magnetic stirrer or mixing with an orbital shaker. According to the invention, mixing can be done, for example, for 1 second to 15 minutes or 10 seconds to 10 minutes.

The present invention also relates to the use of the method of the invention to, for example, identify substances present in a solution, analyse biological samples, perform biological testing, determine blood type, perform immunohematology testing or detect contamination of natural or human origin, for example by viruses, bacteria, amoebae, yeast, cancer cells, prions, pesticides, fungicides, antibiotics, hormones or toxins. The present invention also relates to the use of the method of the invention to, for example, carry out drug testing, conduct scientific studies on substances, for example to study the effect of the solution on the interaction between substances, for example in aqueous solutions, in organic solutions, in gases, for example with molecules, colloids, nanoparticles or microparticles. The present invention also relates to the use of the method of the invention to, for example, perform scientific studies on subjects or substances are involved, for example, in biology, oncology, endocrinology or infectious diseases, for example for the study of hydrogels formed in aqueous solutions, aerogels formed in gases, or gels formed in solvents or in hydrocarbons.

For example, the method of the invention may be used for analysing biological samples, for example for blood serotyping, determining the MHC of an individual or determining the presence, for example, of a particular protein, antibody, or receptor in a sample. The method of the invention may also be used for the identification of chemical substances in a solution.

For example, when the method of the invention is used for serotyping, the solution is a blood sample originating from an individual, for example a human being or an animal, comprising the first substance.

Moreover, the method of the invention may be used for determining the interaction between a receptor and a possible ligand, between an antibody and a protein, a chemical molecule, another antibody and/or any molecule that can be recognized by an antibody. The method of the invention may also be used for detecting the interaction between cells, for example between eukaryotic cells or prokaryotic cells, or between eukaryotic and prokaryotic cells. The method of the invention may also be used for independently detecting the interaction between bacteria, viruses, yeasts and/or eukaryotic cells.

The method of the invention may also be used, for example, to detect phenomena of chemotaxis and cellular adhesion.

The method of the invention may also be used, for example, to detect the interaction between nanoparticles, microparticles or microscale or nanoscale objects of complex shape.

The method of the invention may also be used, for example, to detect the interaction (i) of a first substance, for example antibodies produced by a human or animal in response to an infection, for example by a virus, a bacteria, a prion, a parasite, or a protozoa, as well as in response to a disease, for example cancer, an autoimmune disease such as, for example, Graves' disease, multiple sclerosis, as well as in response to intoxication, poisoning, contamination, doping, ingestion, inhalation or an injection, for example, of a pesticide, a poison, an insecticide, a herbicide, an allergenic agent and also in response to a transplant, for example of bone marrow, an organ such as a kidney, lung or liver, a limb such as a hand, leg or foot, and also in response to implantation of an artificial organ, implantable port, pacemaker, artificial heart or artificial hip and (ii) a second substance, for example a substance that could induce the production of said first substance, for example an antigen responsible for the production of the above-mentioned antibodies.

According to the invention, the solution may comprise the second substance that could have induced the production of said first substance to be detected.

Advantageously, the second substance may be attached to the surface of the container; the attachment of said second substance advantageously permits detecting an interaction between said first and second substances regardless of their concentrations, for example between antibodies and antigens, even when they are present in low quantities.

According to the invention, the method of the invention may also comprise the use (iii) of a third substance.

It may be, for example, a substance such as defined previously, for example antibodies that can recognize at least one of said first and/or second substance. It may be, for example, anti-idiotypic antibodies, for example antibodies specifically recognizing the antibodies produced by a human being or an animal, for example anti-rabbit antibodies, anti-goat antibodies, anti-IgG antibodies, anti-IgM antibodies, anti-IgA antibodies, or anti-IgE antibodies.

According to the invention, the third substance may be attached beforehand to the surface of the container to detect the interaction, for example, of said third substance with said first and/or said second substance.

Advantageously, according to the invention, the third substance is an anti-idiotypic antibody, i.e., an anti-antibody antibody that can interact, for example, with an antibody produced by a human or an animal in response to an antigen and/or an antigen residing or having resided in a human or animal as indicated previously.

The present invention therefore advantageously permits indirectly detecting a substance, for example a substance residing or having resided in a human or animal without needing to develop an antibody interacting specifically with this substance.

The present invention therefore advantageously allows directly or indirectly detecting the presence of antibodies produced in response to an infection, disease, intoxication, poisoning, contamination, doping, ingestion, pesticide or transplant. Moreover, the present invention therefore enables silent infections to be detected, i.e., infections that are not detectable by common microbiological means, for example blood cultures, biopsy cultures, samples of physiological fluid bathing or irrigating the presumed site of infection, for example cerebrospinal fluid, urine, saliva, by detecting, for example, by using anti-idiotypic antibodies interacting with antibodies directed specifically against these infections.

More advantages will appear to a person skilled in the art upon reading the examples below, illustrated by the attached figures, provided for illustration purposes.

EXAMPLES

Example 1: Detecting the Interaction of Antibodies with or without Affinity for Each Other In this example, two strips of 8 flat-bottom wells (Reference: MSW002B, BioFilm Control, France), respectively designated SwH and SwE were used. In each of the strips, 70 µl of an antibody solution were deposited in each of the wells obtained by mixing 15 µl of, respectively, either anti-human IgG antibodies (Reference BI2018, Paris Anticorps, France), or Anti-$E.$ $coli$ antibodies (Reference BP2298, Acris Antibodies, Germany), in 1.5 ml of PBS (8 g/l NaCl (Sigma Aldrich, USA), 200 mg/l KCl (Sigma Aldrich, USA)), 1.44 g/l $Na_2HPO_4$ (Sigma Aldrich, USA), 240 mg/l $KH_2PO_4$ (Sigma Aldrich, USA)) before placing them for 16 hours in a thermostatic oven (Reference BC240, Firelabo, France) stabilized at 37° C.

Solutions designated, respectively, SIg0, SIgH and SIgE, containing 200 µl of a reagent for finding human anti-FY1 anti-red blood cell antibodies (IJB-IH Control 3, reference 108030357, Institut Jacques Boy, France), 2 µl of paramagnetic microbeads (Ton004N, BiofilmControl, France) and, respectively, either 15 µl of water for injection, or 200 µl of anti-human IgG antibodies (Reference BI2018, Paris Anticorps, France), or 200 μl of Anti-*E. coli* antibodies (Reference BP2298, Acris Antibodies GmbH, Germany) were prepared.

The antibody solutions were then removed from the SwH and SwE strips, and then 150 μl of PBS were deposited and removed three times in each well.

100 μl of SIg0, SIgH and SIgE were respectively deposited in wells D, E and F of strips SwH and SwE. The strips were then placed for 20 minutes in a thermostatic oven (Reference BC240, Firelabo, France) stabilized at 37° C., then placed on a magnetized test block (BKT-MSW002 BioFilm Control, France) for 20 seconds. The strips were then placed in a document scanner (Perfection V-750 PRO, Epson, USA) with which a first image was taken with EpsonScan (Epson, USA) software. The magnetization/image capture cycle was reproduced a second time in order to have a second image after a total of 5 minutes of magnetization. The final images were obtained by subtracting the green component of the images from the red component of the color images obtained with the scanner by using ImageJ software (http://rsb.info.nih.gov.ij) and cutting out the images obtained with different contrast adjustments. The corresponding photographs are the images of FIG. 1.

Figure 1:
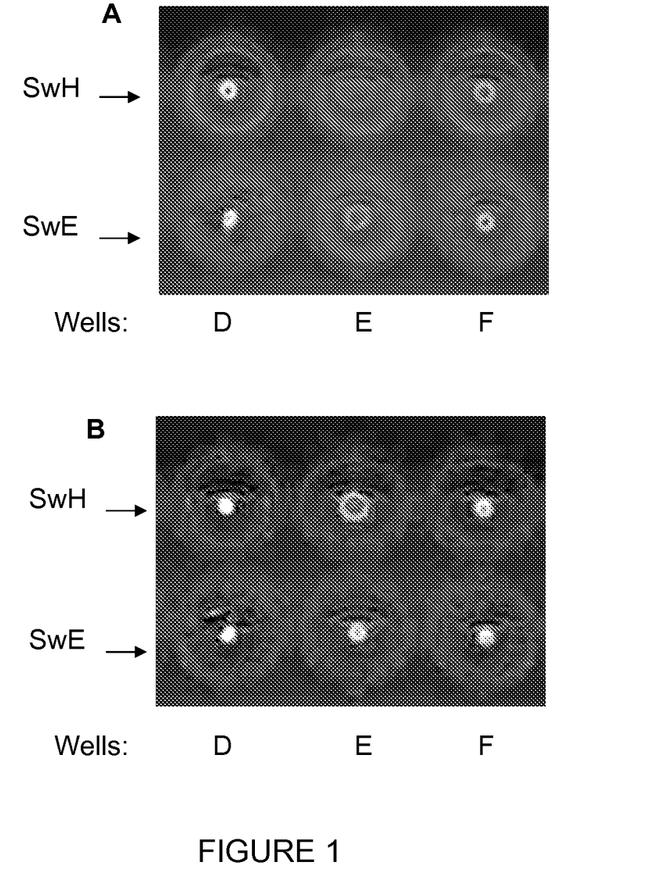
FIG. 1 shows photographs of the spots obtained with antibodies presenting (SwH) or not presenting (SwE) affinity to each other as the affinity substance. Photograph 1A was taken after 20 seconds of magnetizing, photograph 1B after 5 minutes of magnetizing.

Rings of various diameters were obtained, corresponding to the accumulation of beads at the bottom of the well during their migration in the magnetic field. The ring diameter is considered as a measurement according to a decreasing law of magnetic mobility of the beads.

As expected, the diameter of the ring observed in the presence of the expected affinity reaction between the immunoglobulins present in the anti-red blood cell antibody and anti-human Ig antibody research reagents (SwH strip well E) is larger than in the absence of affinity reactions between the immunoglobulins present in the research reagent for anti-red blood cell antibodies and anti-*E. coli* antibodies (SwH strip wells D and F) after 20 seconds of magnetization and in well E, after 5 minutes of magnetization (strips SwH and SwE wells E).

As visible in FIG. 1, well E, this effect is amplified when the two affinity substances are simultaneously present in solution and adsorbed in the well, which greatly reduces the migration of the beads (strip SwH, well E) with regard to the situation, shown in FIG. 1, strip SwH, well D, where one of the substances is only present adsorbed on the surface.

Moreover, when the two affinity substances, i.e., antibodies, are present in solution, if one of the substances is already adsorbed on the surface, the phenomenon of reducing the mobility of the beads is further amplified (wells E, strip SwH compared to SwE).

Finally, when the affinity substance is not adsorbed on the surface, the occurrence of the affinity reaction in the solution is detectable by observing the diameter of the ring formed (strip SwE, well E, compared to wells D and F).

Example 2: Detecting the Interaction Between Anti-Blood Group Determinant Antibodies and Red Blood Cells In this example, three strips of 8 SBS flat-bottom wells (Reference: MSW002B, BioFilm Control, France), respectively designated SwA, SwB and SwAB were used. In each of the wells of the strips, 70 μl of antibody solution, respectively anti A (Reference 102010153, Institut Jacques Boy, France), anti B (102010253, Institut Jacques Boy, France) and anti AB (Reference 102010353, Institut Jacques Boy, France) were deposited.

The strips were placed in a thermostatic oven (Reference BC240, Firelabo, France) stabilized at 37° C. for 10 minutes.

Blood suspensions designated, respectively, hA, hB, hAB and hO, were prepared by diluting 1 ml of TS buffer comprised of 8 g/l NaCl (Sigma-Aldrich, USA) and 1 g/l of tryptone (Difco, USA) with, respectively, 100 μl of red blood cells of type A, B, AB, and O, respectively (IJB-IH Control 2, Reference 108020257, Institut Jacques Boy, France) and 6 μl of paramagnetic microbeads (Ton005N, BiofilmControl, France) and 1 μl of blue food coloring (Vahiné, France).

The antibody solutions were removed from the wells before depositing 70 μl of preparation, hA, hB, hC and hO, respectively, in wells A and B, then C and D, then E and F, then G and H, respectively, of strips SwA, SwB and SwAB.

The strips were placed in a thermostatic oven (Reference BC240, Firelabo, France) stabilized at 37° C. for 10 minutes, then placed on a magnetized test block (BKT-MSW002 BioFilm Control, France) for 1 minute. They were then placed in a document scanner (Perfection V-750 PRO, Epson, USA) with which an image was taken with EpsonScan (Epson, USA) software. The final image was obtained as in Example 1 in FIG. 2.

Figure 2:
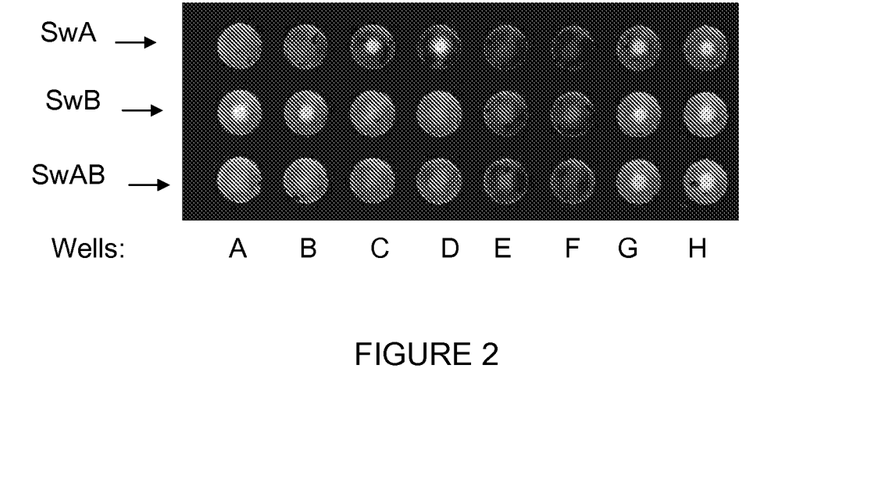
FIG. 2 shows photographs of the spots obtained with anti-blood group determinant antibodies and red blood cells as the affinity substance.

As shown in FIG. 2 in wells C, D, G and H of strip SwA, in wells A, B, G and H of strip SwB and in wells G and H of strip SwAB, the formation of a dark disk was observed of a diameter of around 2 mm±1 mm which was attributed to the absence of affinity reaction between the antibodies bound to the well and the red blood cells. In the other wells, no dark shape is visible, demonstrating an affinity reaction between the antibodies bound to the well and the red blood cells. The observations are summarized in Table 1 below, where the absence of the disk is designated – and the presence of the disk is designated +:

TABLE 1

| | observation of the wells of FIG. 2 | | | | | | | |
|---|---|---|---|---|---|---|---|---|
| | A (hA) | B (hA) | C (hB) | D (hB) | E (hAB) | F (hAB) | G (hO) | H (hO) |
| SwA (anti A) | – | – | + | + | – | – | + | + |
| SwB (anti B) | + | + | – | – | – | – | + | + |
| SwAB (anti AB) | – | – | – | – | – | – | + | + |
| Type deduced | A | A | B | B | AB | AB | O | O |

As demonstrated in this example, the results obtained clearly show the detection of affinity of the antibodies with the corresponding red blood cells. Furthermore, this example clearly shows that the method of the invention enables the serotype of a blood sample to be determined.

Example 3: Detection of the Interaction Between Anti-Determinant Antibodies of Anti-Red Blood Cell Antibodies In this example, two strips of 8 flat-bottom wells (Reference: MSW002B, BioFilm Control, France), designated SwD and SwK, were used. In each of the wells of the strips, 50 μl of a solution obtained by mixing 15 μl of anti-human IgG antibody (Reference BI2018, Paris Anticorps, France) in 1.5 ml of TS buffer (8 g/l NaCl (Sigma Aldrich, USA) and 1 g/l Tryptone (Difco, USA)) were deposited. The strips were then incubated for 16 hours in a thermostatic oven (Reference BC240, Firelabo, France) stabilized at 37° C.

Solutions designated Sp and St, respectively, comprising 150 µl of buffer, respectively PBS and TS, and 0.75 µl of Ton005N were prepared. These solutions are control solutions without red blood cells.

Suspensions designated Si, Sii and Siii, respectively, comprising 150 µl of a red blood cell suspension of type I, II and III (Reference ID-DiaCell I-II-III, Diamed, France) and 0.75 µl of paramagnetic microbeads (Ton005N, BiofilmControl, France) were also prepared.

The antigens present on the surface of the red blood cells were verified by the supplier and are distributed according to Table 2 below:

TABLE 2

| Suspensions | Red blood cells | Duffy | KEL |
| --- | --- | --- | --- |
| Si | Type I red blood cells | + | 0 |
| Sii | Type II red blood cells | + | 0 |
| Siii | Type III red blood cells | 0 | + |

+: presence of antigen, 0: absence of antigen.

Suspensions designated SDi and SKi, SDii and SKii as well as SDiii and SKiii, respectively, comprising 100 µl of a red blood suspension of type I, II and III, respectively (Reference ID-DiaCell I-II-III, Diamed, France), 50 µl of serum, respectively anti FY1 (or anti Duffy) and anti KEL1 (IJB-IH Control 3, reference 108030357, Institut Jacques Boy, France) and 0.75 µl of paramagnetic microbeads (Ton005N, BiofilmControl, France) were also prepared (see Table 3). These suspensions are negative controls comprising red blood cells whose affinity sites are blocked by the antibodies contained in the serums, as well as red blood cell-antibody complexes that no longer have free affinity sites that can bind to the antibodies fixed to the bottom of the well.

TABLE 3

| | Red blood cells | Serum |
| --- | --- | --- |
| SDi | I (D) | Anti FY1 (anti D) |
| SKi | I (D) | Anti KEL1 (anti K) |
| SDii | II (D) | Anti FY1 (anti D) |
| SKii | II (D) | Anti KEL1 (anti K) |
| SDiii | III (K) | Anti FY1 (anti D) |
| SKiii | III (K) | Anti KEL1 (anti K) |

The anti-human IgG antibody solution was then removed from strips SwD and SwK and 150 µl of TS buffer were deposited and removed twice. In each of the wells of strips SwD and SwK, 50 µl of anti-red blood cell antibody research reagents were deposited, respectively anti-FY1 (or anti Duffy) and antiKEL1 (IJB-IH Control 3, reference 108030357, Institut Jacques Boy, France). The strips were then placed in a thermostatic oven (Reference BC240, Firelabo, France) stabilized at 37° C. for 10 minutes.

The solutions of anti-red blood cell antibody research reagents were then removed from strips SwD and SwK and 150 µl of TS buffer were deposited and removed twice.

70 µl of different suspensions were deposited as indicated in Table 4 below:

TABLE 4 distribution of the deposition of the different suspensions

| | A | B | C | D | E | F | G | H |
| --- | --- | --- | --- | --- | --- | --- | --- | --- |
| SwD | Si | Sii | Siii | Sp | St | SDi | SDii | SDiii |
| SwK | Si | Sii | Siii | Sp | St | SKi | SKii | SKiii |

The strips were then placed for 20 minutes in a thermostatic oven (Reference BC240, Firelabo, France) stabilized at 37° C., then placed on a magnetized test block (BKT-MSW002 BioFilm Control, France) for 30 seconds. The strips were then placed in a document scanner (Perfection V-750 PRO, Epson, USA) with which an image was taken with EpsonScan (Epson, USA) software. This image is used to analyse the SwK strip. The magnetization/image capture cycle was reproduced a second time so as to also have an image after a total of one minute of magnetization for the analysis of strip SwD. The final images were obtained as in Example 1 and are shown in FIG. 3.

Figure 3:
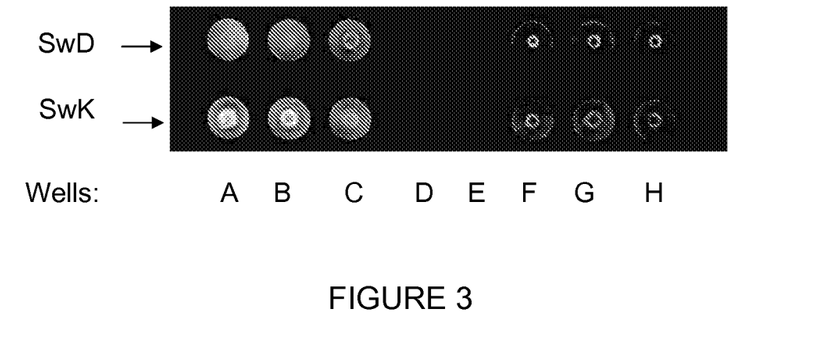
FIG. 3 shows images of the spots obtained with anti-blood group determinant antibodies and red blood cells as the affinity substance.

FIG. 3 shows that a perfectly defined ring is visible in control wells D and E, demonstrating a significant mobility of the paramagnetic beads, a similar ring is obtained in wells F, G and H, demonstrating that a significant mobility is conserved in the presence of red blood cells whose affinity sites are blocked by the antibodies contained in the serums.

The presence of the following can be verified in wells A, B and C:
 either a ring comparable to those of wells F, G and H, indicating a significant mobility attributed to an absence of affinity bonds between the red blood cells and the antibodies bound to the bottom of the well,
 or a diffuse spot indicating a reduced mobility of the paramagnetic beads attributed to an affinity reaction between the antibodies bound to the well and the red blood cells.

Rings and spots are visible according to Table 5 below:

TABLE 5 images obtained

| | A | B | C | D | E | F | G | H |
| --- | --- | --- | --- | --- | --- | --- | --- | --- |
| SwD | spot | spot | ring | ring | ring | ring | ring | ring |
| SwK | ring | ring | spot | ring | ring | ring | ring | ring |

The method of the invention therefore enables the molecular interaction between two substances to be detected.

Example 4: Detecting the Interaction Between Anti-Bacteria Antibodies Present in a Serum and Substances from Bacteria Cultures In this example, two strips of 8 flat-bottom wells (Reference: MSW002B, BioFilm Control, France), respectively designated SwH and SwE are used. In each of the strips, 70 µl of an antibody solution are deposited in each of the wells obtained by mixing 15 µl of, respectively, anti-human IgG antibodies (Reference BI2018, Paris Anticorps, France), and Anti-E. coli antibodies (Reference BP2298, Acris Antibodies, Germany), in 1.5 ml of PBS (8 g/l NaCl (Sigma Aldrich, USA), 200 mg/l KCl (Sigma Aldrich, USA)), 1.44 g/l $Na_2HPO_4$ (Sigma Aldrich, USA), 240 mg/l $KH_2PO_4$ (Sigma Aldrich, USA)) before placing them for 16 hours in a thermostatic oven (Reference BC240, Firelabo, France) stabilized at 37° C. (see Table 6).

TABLE 6

|   | A | B | C | D | E | F | G | H |
|---|---|---|---|---|---|---|---|---|
| SwH | Anti-human | Anti-human | Anti-human | Anti-human | Anti-human | Anti-human | Anti-human | Anti-human |
| SwE | Anti-E. coli | Anti-E. coli | Anti-E. coli | Anti-E. coli | Anti-E. coli | Anti-E. coli | Anti-E. coli | Anti-E. coli |

The IgG solution is then removed from strips SwH and SwE and 150 µl of TS buffer are deposited and removed twice. Deposited in each of the wells A, B, C, D, and E, F, G, H, respectively, of strips SwH and SwE, were 150 µl of human serum originating from, respectively, patients with a *staphylococcus* infection (Staph+serum) and controls without such an infection (Staph−serum) (see Table 7). The strips are then placed in a thermostatic oven (Reference BC240, Firelabo, France) stabilized at 37° C. for 10 minutes.

TABLE 7

|   | A | B | C | D | E | F | G | H |
|---|---|---|---|---|---|---|---|---|
| SwH | Staph + serum/ Anti-human | Staph + serum/ Anti-human | Staph + serum/ Anti-human | Staph + serum/ Anti-human | Staph + serum/ Anti-human | Staph + serum/ Anti-human | Staph + serum/ Anti-human | Staph + serum/ Anti-human |
| SwE | Staph + serum/ Anti-E. coli | Staph + serum/ Anti-E. coli | Staph + serum/ Anti-E. coli | Staph + serum/ Anti-E. coli | Staph + serum/ Anti-E. coli | Staph + serum/ Anti-E. coli | Staph + serum/ Anti-E. coli | Staph + serum/ Anti-E. coli |

50 µl of reagent for detecting *staphylococcus* infection comprising substances from *staphylococcus* cultures and paramagnetic microbeads (Reference: RDS-01R, BioFilm Control, France), are deposited in the wells of the strips.

The strips are then placed for 20 minutes in a thermostatic oven (Reference BC240, Firelabo, France) stabilized at 37° C., then placed on a magnetized test block (BKT-MSW002 BioFilm Control, France) for 10 seconds. The strips are then placed in a document scanner (Perfection V-750 PRO, Epson, USA) with which an image is captured with Epson-Scan (Epson, USA) software. The magnetization/image capture cycle is reproduced a second time in order to also have an image after a total of 5 minutes of magnetization. The final images are obtained as in Example 1.

The diameter of the ring observed in the presence of the expected affinity reaction between the immunoglobulins present in the serum of the infected patient and the substances contained in the reagent for detecting *staphylococcus* (wells A, B, C and D) is greater than in the absence of affinity reaction in the serum of uninfected patients (wells E, F, G and H).

LIST OF REFERENCES

1. U.S. Pat. No. 3,635,678 CLOT-TIMING SYSTEM AND METHOD, Seitz, L. J. and Bowen, J. G.;
2. WO 01/86255, METHOD AND APPARATUS FOR DETERMINING LOCAL VISCOELASTICITY, Cronin-Golomb, M. Shabtai, Y. Nemet, B.;
3. EP1544596, Method and device for determining viscosity, Kurowski D.; Schoen C.; Peters R.; Bartos H.; Yu Y.;
4. Catterall W A. (2000) Structure and regulation of voltage-gated $Ca^{2+}$ channels. *Annu. Rev. Cell. Dev. Biol.* 16:521-55
5. Gerald Karp, Biologie cellulaire et moleculaire, Concepts et experiences [Molecular and Cellular Biology, Concepts and Experiments], $2^{nd}$ edition 2004
6. Dick G M and Tune J D, Role of potassium channels in coronary vasodilation, Exp Biol Med (Maywood). 2010 January; 235(1):10-22
7. Mostallino M C et al. Plasticity and function of extra-synaptic GABA(A) receptors during pregnancy and after delivery, Psychoneuroendocrinology. 2009 December; 34 Suppl 1:S74-83

The invention claimed is:

1. A method for detecting interactions in a solution comprising the following steps:
   a. introducing into a solution at least one first substance and at least one second substance that can interact with said first substance;
   b. introducing into the solution obtained in step a) at least two magnetic or magnetizable particles, said particles resting on a surface immersed in said solution, and said magnetic or magnetisable particles being free within the solution by not being bound to said first substance or said second substance; and
   c. determining an interaction of said first and second substances by application of an electric, magnetic or electromagnetic field designed to set said particles in motion relative to each other, the interaction between said first and second substances being detected when the mobility of said particles on said surface is changed.

2. The method according to claim 1, wherein said at least two magnetic or magnetizable particles are independently an electrically charged, magnetic or magnetizable particle or a particle covered with at least one magnetic or magnetizable layer.

3. The method according to claim 1, wherein said at least two particles are subjected to a pulsed electromagnetic field.

4. The method according to claim 1, wherein the change in the mobility is an acceleration of the movement of particles under the effect of said electric, magnetic or electromagnetic field.

5. The method according to claim 1, wherein the change in the mobility is a slowing of the movement of the particles under the effect of said electric, magnetic or electromagnetic field.

6. The method according to claim 1, wherein the change in the mobility is a change in trajectory of the particles under the effect of said electric, magnetic or electromagnetic field.

7. The method according to claim 1, wherein the interaction is detected by clustering of the particles under the effect of said electric, magnetic or electromagnetic field.

8. The method according to claim 1, wherein the interaction is detected by non-clustering of the particles under the effect of said electric, magnetic or electromagnetic field.

9. The method according to claim 1, wherein the interaction is detected by dispersion of the particles under the effect of said electric, magnetic or electromagnetic field.

10. The method according to claim 1, wherein said at least two particles are illuminated by means of a luminous source to detect their movement.

11. The method according to claim 1, wherein said at least two particles are signal generators.

12. The method according to claim 1, wherein the first substance is chosen in the group comprising eukaryotic cells, prokaryotic cells, membranes, viruses, proteins, antibodies, antigens, chemical molecules.

13. The method according to claim 1, wherein the second substance is chosen in the group comprising eukaryotic cells, prokaryotic cells, membranes, viruses, proteins, antibodies, antigens, chemical molecules.

14. The method according to claim 1, wherein the method includes, instead of step a),
- a prior step a') of attaching said first substance onto a surface of a container;
- a'') introducing a solution into said container; and
- a''') introducing at least one second substance that can interact with said first substance.

* * * * *